United States Patent
Chak

(10) Patent No.: US 9,259,497 B2
(45) Date of Patent: Feb. 16, 2016

(54) FRAGRANCE CONTAINER AND FRAGRANCE DIFFUSER

(71) Applicant: Lui Lok Chak, Chai Wan (HK)

(72) Inventor: Lui Lok Chak, Chai Wan (HK)

( * ) Notice: Subject to any disclaimer, the term of this patent is extended or adjusted under 35 U.S.C. 154(b) by 218 days.

(21) Appl. No.: 13/870,542

(22) Filed: Apr. 25, 2013

(65) Prior Publication Data

US 2014/0322086 A1 Oct. 30, 2014

(51) Int. Cl.
*A61L 9/00* (2006.01)
*A61L 2/00* (2006.01)

(52) U.S. Cl.
CPC .... *A61L 9/00* (2013.01); *A61L 2/00* (2013.01)

(58) Field of Classification Search
CPC .................................... A61L 2/00; A61L 9/00
USPC ........................................................ 422/124
See application file for complete search history.

(56) References Cited

U.S. PATENT DOCUMENTS

| | | | | |
|---|---|---|---|---|
| 4,743,406 | A * | 5/1988 | Steiner et al. | 261/30 |
| 8,251,299 | B1 * | 8/2012 | Irvin | 239/58 |
| 2002/0090317 | A1 * | 7/2002 | Hardy et al. | 422/5 |
| 2005/0047956 | A1 * | 3/2005 | Samii | 422/5 |
| 2006/0113687 | A1 * | 6/2006 | Castellano | 261/26 |
| 2008/0121734 | A1 * | 5/2008 | Cappellina | 239/44 |

OTHER PUBLICATIONS

Green D. W., & Perry, Perry's Chemical Engineers Handbook, 2008, McGraw-Hill, 10-24.*

* cited by examiner

*Primary Examiner* — Kevin Joyner
*Assistant Examiner* — Holly Mull
(74) *Attorney, Agent, or Firm* — Birch, Stewart, Kolasch & Birch, LLP

(57) ABSTRACT

A fragrance container with a container body provided with a bottom bracket permeable to interior air of the container near a bottom opening. A top cover having a shutter within an interior of the container body near a top opening with a fragrance substance contained in the container body between the bottom bracket and the top cover. An outer peripheral portion of the container body near the bottom opening is covered with an indexing collar for adjusting the degree of opening of an intake port of the container body. A fragrance diffuser includes an air pump, a fragrance container retainer connected to the air pump, and at least one fragrance container received in the retainer. The fragrance containers communicate with each other, wherein each of the fragrance containers contains the same type of fragrance substance with the same smell or a different type of fragrance substance with a different smell.

7 Claims, 6 Drawing Sheets

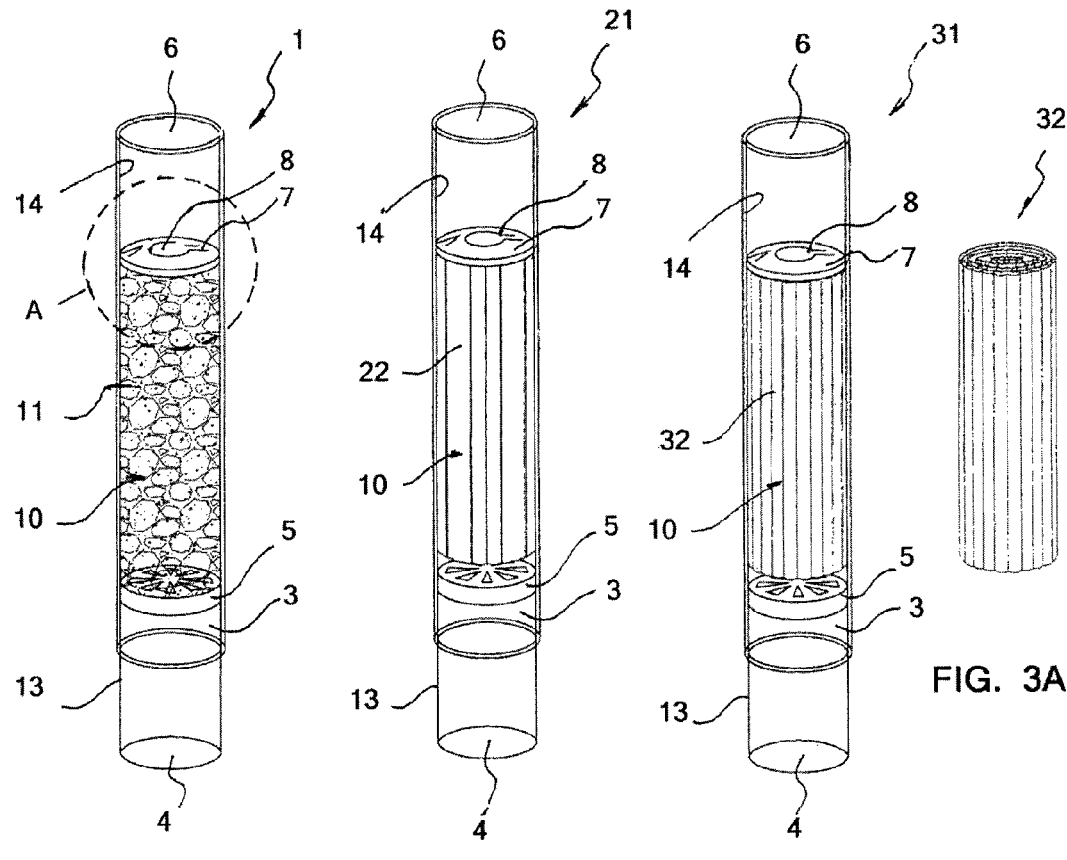
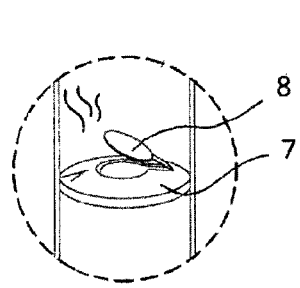
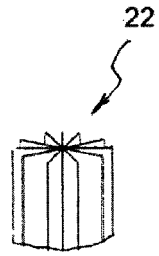
FIG. 1　　　FIG. 2　　　FIG. 3
FIG. 1A　　　FIG. 2A

FRAGRANCE CONTAINER AND FRAGRANCE DIFFUSER

FIELD OF THE INVENTION

The present invention relates to a fragrance diffusion apparatus and, more particularly, relates to a fragrance container adapted for storing and volatizing fragrance substances and a fragrance diffuser.

BACKGROUND OF THE INVENTION

In daily life, people often selectively use fragrance substances or deodorant to generate sweet smell indoor, in order to eliminate stress and fatigue or to eliminate unpleasant smell in toilets and other places. Traditional fragrance diffusers generally realize diffusion of fragrance substances or deodorant by means of heat, wind or ultrasonic atomization. But, they have the following drawbacks. For example, heat sources of diffusers such as scented candles, tea lights, etc., are dangerous due to their open flames. Most wind diffusers are of open-typed, and it is difficult to control the volatilization degree of essential oil in such kind of diffusers. Atomization diffusers need water, and should be cleaned frequently. The above open-typed fragrance diffusers are subject to oil leakage and are not easy to be stored, and cannot control the degree of volatilization and mixing ratio of fragrant smells. Most of the existing closed fragrance diffusers require complicated control methods and complex devices to adjust fragrant smell concentration and mixing ratio, and therefore are expensive and are difficult to operate.

SUMMARY OF THE INVENTION

In view of the above drawbacks, the object of the present invention is to provide a fragrance container which can store a fragrance substance in a closed manner, and which is adapted to volatize the fragrance substance and to generate a fragrance smell when the air is blown into the fragrance container.

The another object of the present invention is to provide an fragrance diffuser, which can adjust the fragrance smell concentration and mixing ratio easily without the need of a complex control method and a large-scale device.

According to a first aspect of the present invention, there is provided a fragrance container, comprising: a container body having a bottom opening, a top opening, an outer peripheral portion near the bottom opening and an inner peripheral portion near the top opening, the container body being provided with a bottom bracket permeable to air within interior of the container body near the bottom opening and a top cover having a shutter within interior of the container body near the top opening; and a fragrance substance contained in the container body between the bottom bracket and the top cover; wherein the fragrance container is adapted to volatilize the fragrance substance and to generate a smell which is then discharged from the top opening of the container body via the shutter when air is blown through the fragrance substance from the bottom opening of the container body.

According to a second aspect of the present invention, there is provided a fragrance cylinder suitable for use in an automobile, comprising: a container body having a bottom opening, a top opening, an outer peripheral portion near the bottom opening and an inner peripheral portion near the top opening, the container body being provided with a bottom bracket permeable to air within interior of the container body near the bottom opening; and fragrance substance contained in the container body above the bottom bracket; wherein the outer peripheral portion of the container body is provided with an intake port for introducing air into the container body; and wherein the outer peripheral portion of the container body is covered with a collar capable of indexing relative to the container body, the collar including a sealed bottom for sealing the bottom opening of the container body and a skirt portion around the container body, the skirt portion having a hole at a position corresponding to the intake port of the container body for adjusting the degree of opening of the intake port of the container body; and wherein the fragrance container is adapted to volatilize the fragrance substance and to generate a smell which is then discharged from the top opening of the container body when air is blown through the fragrance substance from the intake port of the container body.

Preferably, the said container body is configured to be disposed at a front position of an outlet of an automobile air-conditioner so that cold air is blown into the fragrance container through the intake port of the container body.

According to a third aspect of the present invention, there is provided a fragrance diffuser, comprising: an air pump for generating compressed air, the air pump having an suction port and an outlet port; a fragrance container retainer connected to the outlet port through a hose; at least one fragrance container received in the fragrance container retainer, the fragrance container comprising: a container body having a bottom opening, a top opening, an outer peripheral portion near the bottom opening and an inner peripheral portion near the top opening, the container body being provided with a bottom bracket permeable to air within interior of the container body near the bottom opening and a top cover having a shutter within interior of the container body near the top opening; and a fragrance substance contained in the container body between the bottom bracket and the top cover; wherein the fragrance container is adapted to volatilize the fragrance substance and to generate a smell which is then discharged from the top opening of the container body via the shutter when air is blown through the fragrance substance from the bottom opening of the container body.

Preferably, the fragrance diffuser comprises two or more fragrance containers, each of the fragrance containers being configured in such manner that the outer peripheral portion of a container body near the bottom opening can be inserted into the inner peripheral portion of another container body near the top opening to communicate the fragrance containers with each other.

Preferably, the fragrance containers contain the same type of fragrance substance with the same smell.

Preferably, the fragrance containers contain respectively a different type of fragrance substance with different smell.

Preferably, the fragrance substance comprises solid fragrance grains, or fragrant materials in liquid state carried by a star-shaped oil-absorbing cloth, or fragrant materials in liquid state carried by a roll of corrugated paper.

Preferably, the container body has a cross section in a circle or an ellipse shape.

Preferably, the container body is made of glass, plastics or metal.

Preferably, the fragrance diffuser further comprises an electrical control device for controlling the timing of start-up and operation of the air pump.

Preferably, the fragrance diffuser further comprises a cartridge body for accommodating the air pump, the electrical control device and the fragrance container retainer, the fragrance container retainer being fixed on the cartridge body and being communicated to the external of the cartridge body.

According to the fragrance diffuser of the present invention, since each fragrance cylinder contains respectively a fragrance substance having a kind of smell, the replacement of different typed fragrance cylinders is easy. Since the fragrance cylinder is in a closed manner, it can prevent leakage and evaporation of the fragrance substance stored therein when not in use. According to the fragrance diffuser of the present invention, due to the adopting of a stacked connection structure of fragrance cylinder, it is easy to adjust the fragrance smell concentration and the mixed smell and therefore the device is inexpensive and the operation and use thereof are easy.

BRIEF DESCRIPTION OF THE DRAWINGS

The basic structures of various embodiments according to the present invention will be described in details for illustration purpose only, with reference to the accompanying drawings, in which:

FIG. 1 is a perspective view of a first embodiment of a fragrance container according to the present invention;

FIG. 1A is a partial enlarged view of a circled portion A of FIG. 1, showing a shutter on a cover of the first embodiment in an open state;

FIG. 2 is a perspective view of a second embodiment of a fragrance container according to the present invention;

FIG. 2A is a partial perspective view of a star-shaped oil-absorbing cloth shown in FIG. 2;

FIG. 3 is a perspective view of a third embodiment of a fragrance container according to the present invention;

FIG. 3A is a perspective view of a roll of corrugated cardboard shown in FIG. 3;

DESCRIPTION OF THE PREFERRED EMBODIMENTS

Figures 4, 5, 6:
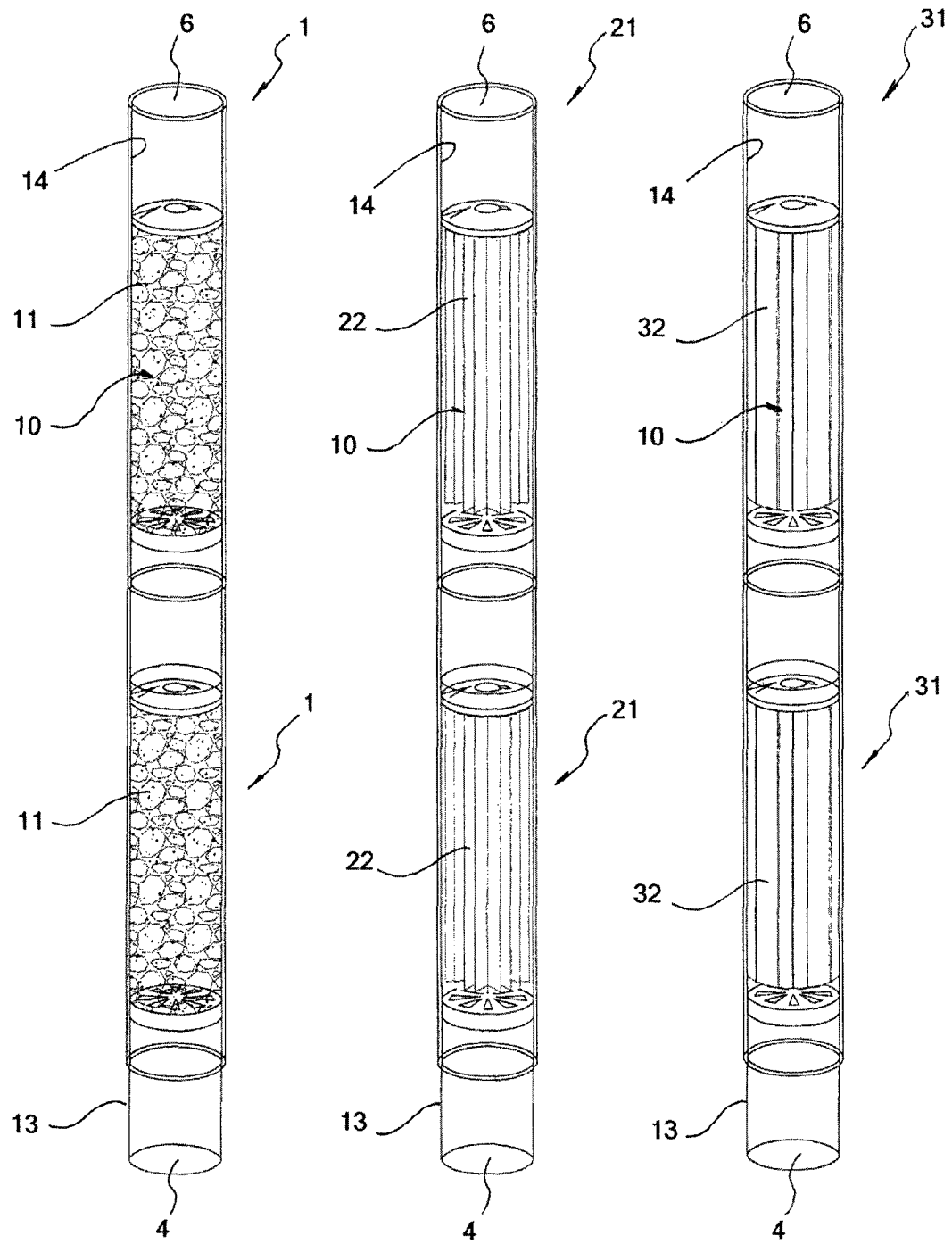
FIG. 4 is a schematic perspective view of two fragrance containers shown in FIG. 1 which communicate with each other.
FIG. 5 is a schematic perspective view of the two fragrance containers shown in FIG. 2 which communicate with each other.
FIG. 6 is a schematic perspective view of the two fragrance containers as shown in FIG. 3 which communicate with each other.

Various embodiments of the fragrance container and the fragrance diffuser according to the present invention are described for illustration purpose with reference to the drawings, but the present invention is not limited thereto. In each of the following embodiments, the same components are marked with the same reference numerals.

FIG. 1 shows a basic structure of a first embodiment of a fragrance container according to the present invention. As shown in FIG. 1, the fragrance container 1 comprises a container body 3 provided with a bottom opening 4 and a top opening 6, a bottom bracket 5 permeable to air and provided within interior of the container body 3 near the bottom opening 4 and a top cover 7 provided within interior of the container body 3 near the top opening 6. The top cover 7 is provided with a shutter 8. In the interior of the container body 3, fragrance substance 10 is contained between the bottom bracket 5 and the top cover 7. FIG. 1A shows the shutter 8 on the top cover 7 in an open state. In the illustrated embodiments, the cross section of the container body 3 could be in the shape of a circle, an ellipse or other suitable shape. The container body 3 is made of glass, plastics or metal. Each of the fragrance containers of the present invention is suitable for respectively containing a kind of fragrance substance with respective smell. The fragrance substances can be of solid material, but can also be of liquid material carried by an absorbent carrier. For example, as shown in FIG. 1, the fragrance substance 10 is fragrant grains 11. The fragrance container 1 is adapted to volatilize the fragrance substance 10 and to generate a smell which is then discharged from the top opening 6 of the container body 3 via the shutter 8 when air is blown from the bottom opening 4 of the container body through the fragrance substance. An outer peripheral portion 13 of the container body 3 near the bottom opening 4 is configured in such a manner that it could be inserted into an inner peripheral portion 14 of the container body 3 near the top opening 6. When in use, the outer peripheral portion 13 of a container body 3 near the bottom opening 4 can be inserted into a fragrance container retainer 69 (see FIG. 8), or can be inserted into the inner peripheral portion 14 of another container body 3 near the top opening to communicate with each other.

FIG. 2 shows a basic structure of a second embodiment of a fragrance container according to the present invention. As shown in FIG. 2, the fragrance substance 10 contained in the container body 21 is in liquid state carried by a star-shaped oil-absorbing cloth 22. FIG. 2A shows a part of the star-shaped oil-absorbing cloth 22. In this embodiment, the other parts or elements of the fragrance container 21 are basically same as those of the first embodiment, and thus detailed description thereof is omitted herein.

FIG. 3 shows a basic structure of a third embodiment of a fragrance container according to the present invention. As shown in FIG. 3, the fragrance substance 10 contained in the cylinder body 31 is in liquid state carried by a roll of corrugated paper. FIG. 3A shows a general shape of a roll of corrugated paper 32. In this embodiment, the other parts or elements of the fragrance container 31 are basically same as those of the first embodiment, and thus detailed description thereof is omitted herein.

FIGS. 4, 5 and 6 show respectively the state of two fragrance cylinders 1, 21 and 31 shown respectively in FIGS. 1, 2 and 3 communicating with each other, wherein the outer peripheral portion 13 of the container body 3 near the bottom opening 4 of each fragrance container 1, 21 and 31 is inserted into the inner peripheral portion 14 of the container body 3 near the top opening of another fragrance container 1, 21 and 31. According to the present invention, as can be seen in the drawings, fragrance containers containing the same type of fragrance substance with the same smell could communicate with each other so as to increase the concentration of the smell when air is blown through the fragrance substance 10. Similarly, fragrance containers containing different types of fragrance substances with different smells could communicate with each other so as to obtain a required mixed smell when air is blown through the fragrance substances 10.

Figure 7:
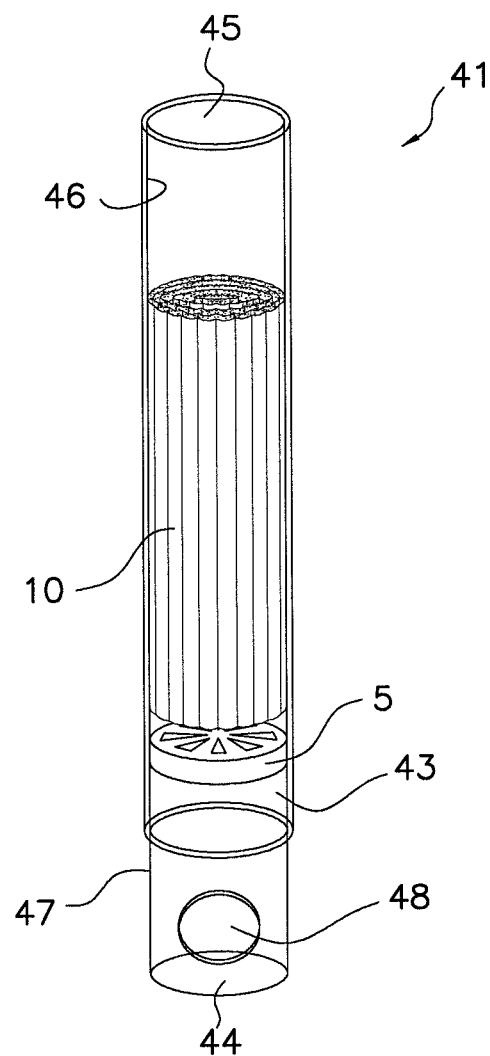
FIG. 7 is an exploded perspective view of a fourth embodiment of a fragrance container according to the present invention.
Figure 7:
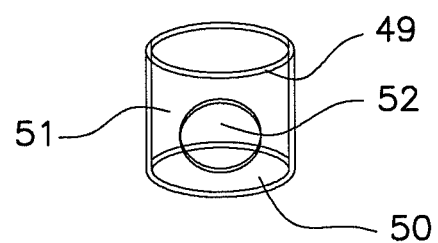

FIG. 7 shows a basic structure of a fourth embodiment of a fragrance container according to the present invention. In this embodiment, the structure of the fragrance container 41 is basically the same as that of the first embodiment, except for omission of the top cover 7 with a shutter 8 and a minor difference in the structure of the container body 43. As shown in FIG. 7, the container body 43 has a bottom opening 44, a top opening 45, an inner peripheral portion 46 near the top opening 45 and an outer peripheral portion 47 near the bottom opening 44. In interior of the container body 43, the fragrance substance 10, for example fragrant materials in liquid state carried by a roll of corrugated paper, is contained above the bottom bracket 5. The outer peripheral portion 47 of the container body 43 near the bottom opening 44 is provided with an intake port 48 for introducing air into the container body 43. Furthermore, the outer peripheral portion 47 of the container body 43 near the bottom opening 44 is covered with a collar 49 which is capable of indexing relative to the container body 43. The collar 49 includes a sealed bottom 50 for sealing the bottom opening 44 of the container body 43 and a skirt portion 51 around the outer peripheral portion 47 of the container body 43 near the bottom opening 44. The skirt portion 51 has a hole 52 at a position corresponding to the intake port 48 of the container body 43 for adjusting the degree of opening of the intake port 48 of the container body 43 when the collar 49 indexes relative to the container body 43. The fragrance container 41 is suitable for use in an automobile. For example, it is adapted to be disposed at a front position of an outlet of an automobile air-conditioner so that cold air is blown into the fragrance container 41 through the intake port 48 of the container body 43.

Figure 8:
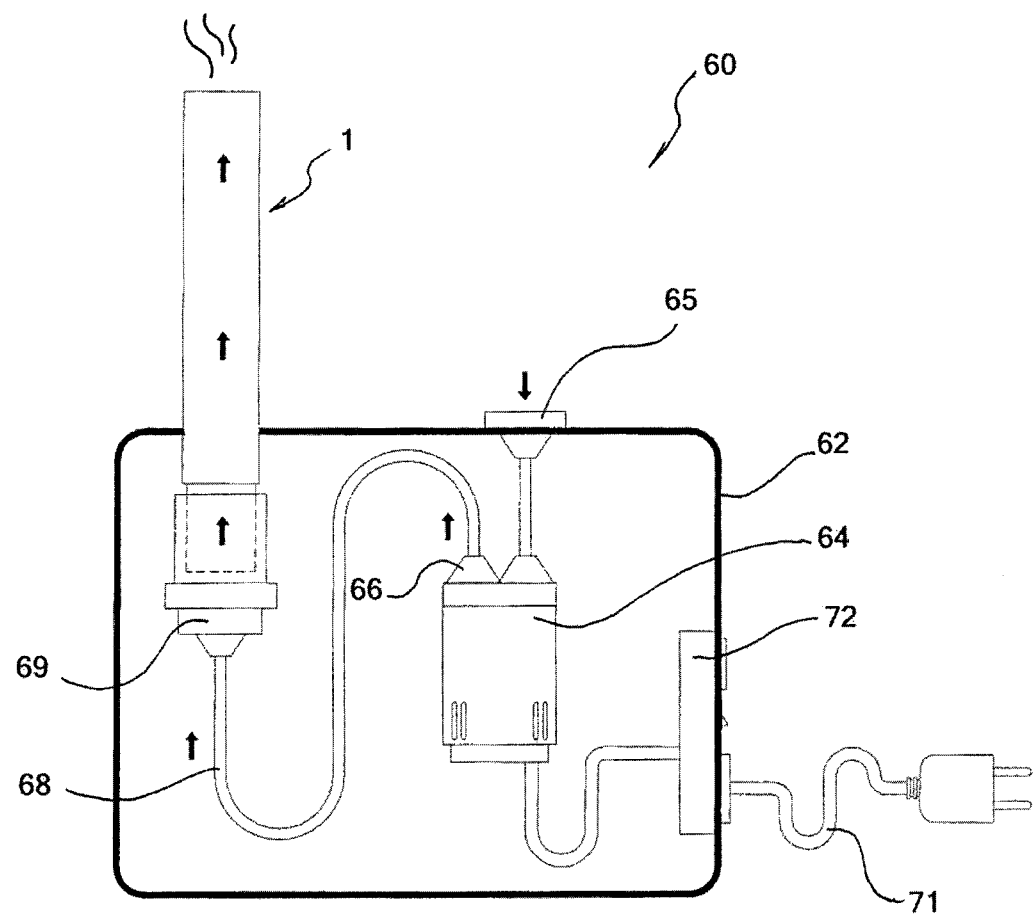
FIG. 8 is a schematic structural view of a fragrance diffuser according to the present invention.
Figure 9:
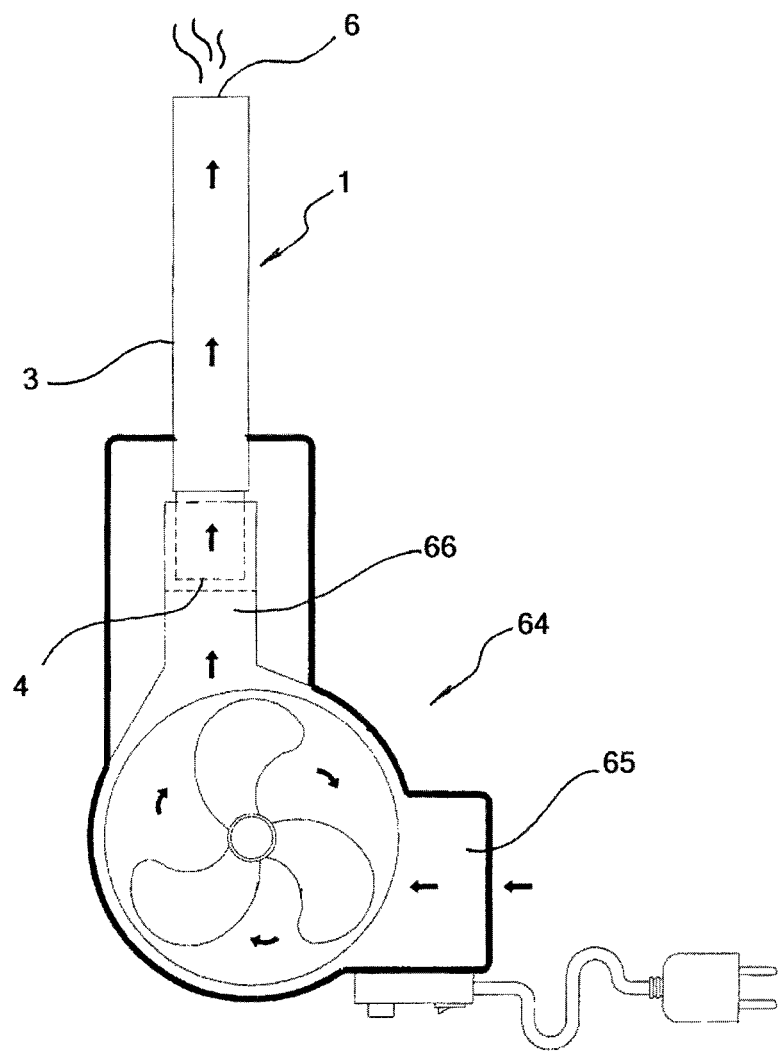
FIG. 9 is an explanatory diagram illustrating the operation of the fragrance diffuser shown in FIG. 8.
Figure 10:
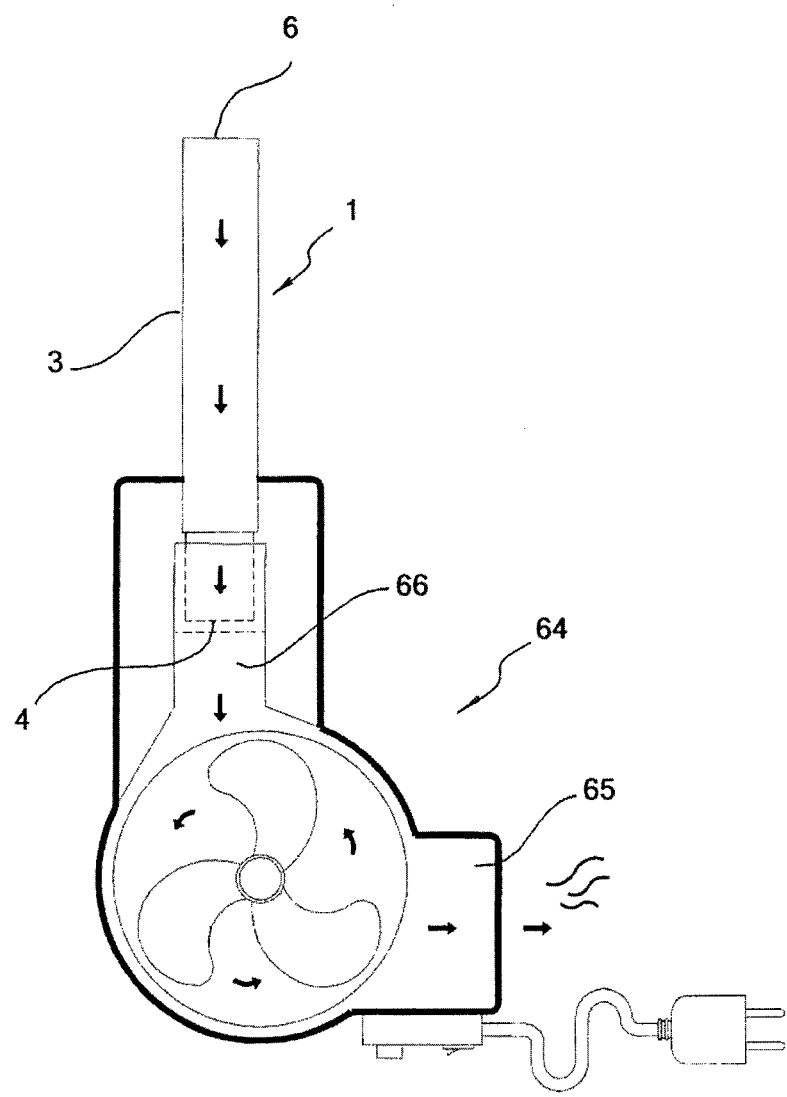
FIG. 10 is another explanatory diagram illustrating the operation of the fragrance diffuser shown in FIG. 8.

The basic structure of a fragrance diffuser of the present invention will be described below with reference to FIG. 8. As shown in FIG. 8, the fragrance diffuser 60 comprises a cartridge body 62. An air pump 64 is provided in the cartridge body 62 for generating compressed air. The air pump 64 has a suction port 65 and an outlet port 66 connected through a hose 68 to the fragrance container retainer 69. The fragrance container retainer 69 is fixed on the cartridge body 62 and is communicated to the external of the cartridge body 62 for receiving one fragrance cylinder 1, 21, 31 or more fragrance cylinders 1, 21, 31 communicating with each other. Only a single fragrance cylinder 1 is schematically illustrated in FIG. 8. The air pump 64 is connected to a power supply (not shown), and the timing of start-up and operation of the air pump 64 is controlled by an electrical control device 72. As shown in FIG. 9, when the air pump 64 is operated, air is sucked from the suction port 65, and compressed air is discharged from the outlet port 66 and is blown through the fragrance substance from the inlet 4 of the container body 3 to volatilize fragrance substance 10 therein and to generate smell which is then discharged from the top opening 6 of the container body 3. It is understood that the air pump 64 can be operated in a reverse direction. As shown in FIG. 10, when the air pump 64 is operated in a reverse direction, the gas stream flows reversely, and therefore the arrangement position of the air intake and the smell discharged of the fragrance diffuser 60 can be changed as needed.

The fragrance diffuser 60 of the present invention, when in use, two or more fragrance containers 1, 21, 31 containing the same type of fragrance substance with the same smell can communicate with each other so as to increase the concentration of the smell. Similarly, two or more fragrance containers containing respectively a different type of fragrance substance with different smell can communicate with each other so as to adjust easily the mixing smell as needed.

In summary, according to the present invention, each fragrance container contains respectively fragrance substance having a kind of smell such that the replacement of different typed fragrance containers is easy. The fragrance container is closed, it can prevent leakage and evaporation of the fragrance substances stored therein when not in use. In the fragrance diffuser according to the present invention, the opening and closing of the shutter on the top cover of the fragrance container is follow the startup of the air pump and therefore a solenoid valve used for turning off the fragrance diffuser can be omitted. The adopting of a stacked connection structure of fragrance container facilitates to adjust the fragrance smell concentration and the mixing smell. Therefore, the fragrance diffusion apparatus of the present invention does not require complicated control methods and complex devices and is inexpensive and easy to operate and use.

What is claimed is:

1. A fragrance creating container system comprising:
    a fragrance container body having an outer surface and an inner surface defining an inlet end and an outlet end, for channeling an airflow along an axis from the inlet end to the outlet end, said inner surface of the container extending beyond the outer surface thereof, at said inlet end, and containing an aperture and a skirt or collar having a sealed bottom slidably attached to the inner surface of the container body at the inlet end, said collar having an aperture which is adapted to align with the aperture in the extended inner surface of the container for adjusting the airflow through the container body,
    a bracket, permeable to said airflow and disposed in the container body near the inlet end,
    a shutter disposed near the outlet end for varying the airflow from the outlet end,
    at least one fragrance substance positioned within the container body between the bracket and the shutter, said fragrance substance being contained as a unit, and a plurality of units stacked end-to-end to form a stacked configuration so that the airflow will traverse the entirety of the stacked configuration,
    an air pump,
    an electrical control system operatively connected to the air pump and capable of selectively producing a positive or negative air flow through the fragrance container body, and
    a flexible conduit for providing communication between the air pump and the inlet end of the fragrance container body,
    wherein airflow through the fragrance substance disposed in the container body generates a fragrance which is discharged from the outlet end of the container body.

2. The fragrance container according to claim 1, wherein the fragrance substance comprises solid fragrant grains, fragrant materials in a liquid state carried by a star-shaped oil-absorbing cloth or a roll of corrugated paper.

3. The fragrance container according to claim 1, wherein the container body has an elliptical or circular cross section.

4. The fragrance container according to claim 1, wherein the container body is made of glass, plastics or metal.

5. The fragrance container according to claim 1, wherein the container body is configured to be disposed at a front position of an outlet of an automobile air-conditioner so that cold air is blown into the fragrance container through the intake port of the container body.

6. The fragrance diffuser according to claim 1, wherein the fragrance containers contain the same type of fragrance substance with the same smell or different type of fragrance substances with different smells.

7. The fragrance diffuser according to claim 1, wherein the electrical control system controls the timing of start-up and operation of the air pump.

* * * * *